US006828091B2

(12) United States Patent
Kasibhatla et al.

(10) Patent No.: US 6,828,091 B2
(45) Date of Patent: Dec. 7, 2004

(54) METHOD OF IDENTIFYING IMMUNOSUPPRESSIVE AGENTS

(75) Inventors: Shailaja Kasibhatla, San Diego, CA (US); Douglas R. Green, San Diego, CA (US); Ben Tseng, San Diego, CA (US)

(73) Assignee: Cytovia, Inc., San Diego, CA (US)

( * ) Notice: Subject to any disclaimer, the term of this patent is extended or adjusted under 35 U.S.C. 154(b) by 87 days.

(21) Appl. No.: 09/920,332

(22) Filed: Aug. 2, 2001

(65) Prior Publication Data

US 2002/0076733 A1 Jun. 20, 2002

Related U.S. Application Data

(60) Provisional application No. 60/222,897, filed on Aug. 3, 2000.

(51) Int. Cl.[7] .................. C12Q 1/25; G01N 33/533; G01N 33/573
(52) U.S. Cl. .................. 435/4; 435/7.24; 435/7.72; 435/7.92
(58) Field of Search .................. 435/4, 7.24, 7.72, 435/7.92, 69.2

(56) References Cited

U.S. PATENT DOCUMENTS

| | | |
|---|---|---|
| 4,336,186 A | 6/1982 | Gargiulo et al. |
| 4,557,862 A | 12/1985 | Mangel et al. |
| 4,640,893 A | 2/1987 | Mangel et al. |
| 5,208,148 A | 5/1993 | Haugland et al. |
| 5,227,487 A | 7/1993 | Haugland et al. |
| 5,362,628 A | 11/1994 | Haugland et al. |
| 5,443,986 A | 8/1995 | Haughland et al. |
| 5,556,992 A | 9/1996 | Gaboury et al. |
| 5,576,424 A | 11/1996 | Mao et al. |
| 5,587,490 A | 12/1996 | Goodrich, Jr. et al. |
| 5,605,809 A | 2/1997 | Komoriya et al. |
| 5,698,411 A | 12/1997 | Lucas et al. |
| 5,714,342 A | 2/1998 | Komoriya et al. |
| 5,733,719 A | 3/1998 | Jaffe et al. |
| 5,773,236 A | 6/1998 | Diwu et al. |
| 5,776,720 A | 7/1998 | Jaffe et al. |
| 5,834,216 A | 11/1998 | Roizman et al. |
| 5,843,635 A | 12/1998 | Schlossman et al. |
| 5,849,513 A | 12/1998 | Jaffe et al. |
| 5,871,946 A | 2/1999 | Lucas et al. |
| 5,897,992 A | 4/1999 | Fearnhead et al. |
| 5,908,750 A | 6/1999 | Reed et al. |
| 5,976,822 A | 11/1999 | Landrum et al. |
| 6,075,020 A | 6/2000 | Cincotta et al. |
| 6,077,684 A | 6/2000 | Kravtsov |
| 6,200,969 B1 | 3/2001 | Fritz et al. |
| 6,248,904 B1 | 6/2001 | Zhang et al. |
| 6,251,614 B1 | 6/2001 | Fritz et al. |
| 6,270,980 B1 | 8/2001 | Fritz et al. |
| 6,335,429 B1 | 1/2002 | Cai et al. |
| 6,342,611 B1 | 1/2002 | Weber et al. |
| 2002/0150885 A1 | 10/2002 | Weber et al. |
| 2003/0027229 A1 | 2/2003 | Kasibhatla et al. |

FOREIGN PATENT DOCUMENTS

| | | |
|---|---|---|
| CA | 2119840 | 9/1994 |
| EP | 0 285 179 B1 | 6/1993 |
| WO | WO 93/10461 | 5/1993 |
| WO | WO 96/20721 | 7/1996 |
| WO | WO 98/55863 | 6/1998 |
| WO | WO 98/57664 | 12/1998 |
| WO | WO 99/18856 | 4/1999 |
| WO | WO 00/07017 | 2/2000 |
| WO | WO 00/45165 | 8/2000 |
| WO | WO 01/79187 A2 | 10/2001 |
| WO | WO 02/12545 A2 | 2/2002 |

OTHER PUBLICATIONS

Porter et al, Analytical Biochemistry 123(1): 41–48, 1982.*
Evans et al, Cancer Research 54: 1596–1603, Mar. 1994.*
Wesselborg et al, Eur J Immunol 23(10): 2707–10, Oct. 1993.*
Zeher et al, Arthritis Rheum 43(5): 1187–8, May 2000.*
Lesage et al, J Immunol 159(10): 4762–71, Nov. 1997.*
Bradbury et al, J Immunol Methods 240(1–2): 79–92, Jun. 2000.*
Stryer et al, in Biochemistry, Third edition, W H Freeman Company, New York, pp. 31–33, 1998.*
Migita et al, Transplantation 64(9): 1365–9, Nov. 1997.*
Biomol. Research Laboratories, Inc., "Apoptosis Inducers and the Assay of Caspase Activity," *FASEB J. 12*:A1488, Abstract No. T10, Federation of American Societies for Experimental Biology (1998).
Hug, H. et al., "Rhodamine 110–Linked Amino Acids and Peptides as Substrates to Measure Caspase Activity upon Apoptosis Induction in Intact Cells," *Biochem.* 38: 13906–13911, American Chemical Society (Oct. 1999).
Jones, J. et al., "Development and Application of a GFP–FRET Intracellular Caspase Assay for Drug Screening," *J. Biomol. Screening 5*:307–317, The Society for Biomolecular Screening (Oct. 2000).
Leoni, L.M. et al., "Indanocine, a Microtubule–Binding Indanone and a Selective Inducer of Apoptosis in Multi-drug–Resistant Cancer Cells," *J. Natl. Canc. Inst.* 92:217–224, Oxford University Press (Feb. 2000).

(List continued on next page.)

Primary Examiner—Christina Chan
Assistant Examiner—Phuong Huynh
(74) *Attorney, Agent, or Firm*—Sterne, Kessler, Goldstein & Fox P.L.L.C.

(57) ABSTRACT

A method for identifying therapeutically effective immunosuppressive agents by screening such agents for those which induce apoptosis in activated T cells is disclosed. T cells were isolated then activated and treating with various test compounds. A caspase substrate is added to detect caspase activation and apoptosis in the cells. Compounds which stimulate caspase activation and apoptosis are also tested against resting T cells to determine those agents which are more effective in activated T cells compared to resting T cells. Compounds with this selectivity are effective in treating immunopathological disorders such as arthritis, graft rejection, graft versus host disease, inflammatory bowel syndrome and the like.

24 Claims, 5 Drawing Sheets

OTHER PUBLICATIONS

Monks, A. et al., "Feasibility of a High–Flux Anticancer Drug Screen Using a Diverse Panel of Cultured Human Tumor Cell Lines," *J. Natl. Canc. Inst.* 83:757–766, Oxford University Press (1991).

Mooberry, S.L. et al., "Laulimalide and Isolaulimalide, New Paclitaxel–Like Microtubule–Stabilizing Agents," *Canc. Res.* 59:653–660, American Society for Cancer Research (Feb. 1999).

Tepper, A. D. et al., "CD95/Fas–induced Ceramide Formation Proceeds with Slow Kinetics and is not Blocked by Caspase–3/CPP32 Inhibition," *J. Biol. Chem.* 272:24308–24312, The American Society for Biochemistry and Molecular Biology, Inc., (1997).

Zhou, T. et al., "Bisindolylmaleimide VIII facilitates Fas–mediated apoptosis and inhibits T cell–mediated autoimmune diseases," *Nat. Med.* 5:42–48, Nature Publishing Company (Jan. 1999).

International Search Report for International Application No. PCT/US01/24250 (published as document AM3), mailed May 31, 2002.

Co–pending U.S. patent application No. 10/046,548, Kasibhatla, S. et al., filed Jan. 16, 2002.

Assfalg–Machleidt, I., et al., "Membrane Permeable Fluorogenic Rhodamine Substrates for Selective Determination of Cathepsin L," *Biol. Chem. Hoppe–Seyler* 373:433–440, Walter de Gruyter & Co. (1992).

Bonneau, P., et al., "Design of Fluorogenic Peptide Substrates for Human Cytomegalovirus Protease Based on Structure–Activity Relationship Studies," *Anal. Biochem.* 255:59–65, Academic Press, Inc. (1998).

DiIanni, C.L., et al., "In Vitro Activity of the Herpes Simplex Virus Type 1 Protease with Peptide Substrates," *J. Biol. Chem.* 268:25449–25454, American Society for Biochemistry and Molecular Biology, Inc. (1993).

Dinarello, C.A., "Interleukin–1 and Interleukin–1 Antagonism," *Blood* 77:1627–1652, The American Society of Hematology (1991).

Friesen, C., et al., "Involvement of the CD95 (APO–1/Fas) receptor/ligand system in drug–induced apoptosis in leukemia cells," *Nat. Med.* 2:574–577, Nature Publishing Group (1996).

Fulda, S., et al., "Betulinic Acid Triggers CD95 (APO–1/FAS)—and p53–independent Apoptosis via Activation of Caspases in Neuroectodermal Tumors," *Canc. Res.* 57:4956–4964, American Association for Cancer Research (1997).

Gallop, M.A., et al., "Applications of Combinatorial Technologies to Drug Discovery. 1. Background and Peptide Combinatorial Libraries," *J. Med. Chem.* 37:1233–1251, American Chemical Society (1994).

Gamen, S., et al., "Doxorubicin–induced apoptosis in human T–cell leukemia is mediated by caspase–3 activation in a Fas–independent way," *FEBS Lett.* 417:360–364, Elsevier Science B.V. (1997).

Ganesh, S., et al., "Flow Cytometric Determination of Aminopeptidase Activities in Viable Cells Using Fluorogenic Rhodamine 110 Substrates," *Cytometry* 20:334–340, Wiley–Liss, Inc. (1995).

Gordon, E.M., et al., "Applications of Combinatorial Technologies to Drug Discovery. 2. Combinatorial Organic Synthesis, Library Screening Strategies, and Future Directions," *J. Med. Chem.* 37:1385–1401, American Chemical Society (1994).

Hardin, J.A., et al., "A simple fluorescence method for surface antigen phenotyping of lymphocytes undergoing DNA fragmentation," *J. Immunol. Meth.* 154:99–107, Elsevier Science Publishers B.V. (1992).

Haugland, R.P. and Johnson, I.D., "Detecting Enzymes in Living Cells Using Fluorogenic Substrates," *J. Fluorescence* 3:119–127, Plenum Publishing Corporation (1993).

Haugland, R.P., "Detecting Enzymatic Activity in Cells Using Fluorogenic Substrates," *Biotechnic & Histochemistry* 70:243–251, Williams & Wilkins (1995).

Haugland, R.P., *Handbook of Fluorescent Probes and Research Chemicals, 6$^{th}$ Ed.*, Spence, M.T.Z., ed., Molecular Probes, Inc., Eugene, Oregon, pp. 28, 54, 225–234 (1996).

Hickman, J.A., "Apoptosis induced by anticancer drugs," *Cancer Metastasis Rev.* 11:121–139, Kluwer Academic Publishers (1992).

Holskin, B.P., et al., "A Continuous Fluorescence–Based Assay of Human Cytomegalovirus Protease Using a Peptide Substrate," *Anal. Biochem.* 226:148–155, Academic Press, Inc. (1995).

Johnson, A.F., et al., "Nonisotopic DNA Detection System Employing Elastase and a Fluorogenic Rhodamine Substrate," *Anal. Chem.* 65:2352–2359, American Chemical Society (1993).

Klingel, S., et al., "Flow Cytometric Determination of Cysteine and Serine Proteinase Activities in Living Cells with Rhodamine 110 Substrates," *Meth. Cell Biol.* 41:449–459, Academic Press, Inc. (1994).

Leytus, S.P., et al., "New class of sensitive and selective fluorogenic substrates for serine proteinases," *Biochem. J.* 215:253–260, The Biochemical Society (1983).

Leytus, S.P., et al., "Rhodamine–based compounds as fluorogenic substrates for serine proteinases," *Biochem. J.* 209:299–307, The Biochemical Society (1983).

Los, M., et al., "Requirement of an ICE/CED–3 protease for Fas/APO–1–mediated apoptosis," *Nature* 375:81–83, Nature Publishing Group (1995).

Los, M., et al., "Cross–Resistance of CD95– and Drug–Induced Apoptosis as a Consequence of Deficient Activation of Caspases (ICE/Ced–3 Proteases)," *Blood* 90:3118–3129, American Society of Hematology (1997).

Matayoshi, E.D., et al., "Novel Fluorogenic Substrates for Assaying Retroviral Proteases by Resonance Energy Transfer," *Science* 247:954–958, American Association for the Advancement of Science (1990).

Mohr, S., et al., "Macrophage resistant to endogenously generated nitric oxide–mediated apoptosis are hypersensitive to exogenously added nitric oxide donors: Dichotomous apoptotic response independent of caspase 3 and reversal by the mitogen–activated protein kinase kinase (MEK) inhibitor PD 098059," *Proc. Natl. Acad. Sci. USA* 95:5045–5050, National Academy of Sciences (1998).

Molecular Probes, Inc., "Alphabetical Price List of New Products Jan. 1994," Molecular Probes, Inc., Eugene, Oregon, pp. 1–4 (1994).

Morliere, P., et al., "Interaction of Tetrapyrrolic Rings with Rhodamine 110 and 123 and with Rhodamine 110 Derivatives Bearing A Peptide Side Chain," *Biochem. Biophys. Res. Comm.* 146:107–113, Academic Press, Inc. (1987).

O'Boyle, D.R., et al., "Identification of a Novel Peptide Substrate of HSV–1 Protease Using Substrate Phage Display," *Virology* 236:338–347, Academic Press, Inc. (1997).

Qi, X.–M., et al., "Baculovirus p35 and Z–VAD–fmk inhibit thapsigargin–induced apoptosis of breast cancer cells," *Oncogene* 15:1207–1212, Stockton Press (1997).

Richards, A.D., et al., "Sensitive, Soluble Chromogenic Substrates for HIV–1 Proteinase," *J. Biol. Chem.* 265:7733–7736, American Society for Biochemistry and Molecular Biology, Inc. (1990).

Rothe, G., et al., "Flow Cytometric Analysis of Protease Activities in Vital Cells," *Biol. Chem. Hoppe–Seyler* 373:547–554, Walter de Gruyter & Co. (1992).

Stevens, J.T., et al., "In vitro proteolytic activity and active site identification of the human cytomegalovirus protease," *Eur. J. Biochem.* 226:361–367, Springer International (1994).

Tamburini, P.P., et al., "A Fluorometric Assay for HIV–Protease Activity Using High–Performance Liquid Chromatography," *Anal. Biochem.* 186:363–368, Academic Press, Inc. (1990).

Thornberry, N.A., et al., "A Combinatorial Approach Defines Specificities of Members of the Caspase Family and Granzyme B," *J. Biol. Chem.* 272:17907–17911, The American Society for Biochemistry and Molecular Biology, Inc. (1997).

Thornberry, N.A., "Caspases: key mediators of apoptosis," *Chem. Biol.* 5:R97–R103, Current Biology Ltd. (1998).

Toth, M.V. and Marshall, G.R., "A simple, continuous fluorometric assay for HIV protease," *Int. J. Peptide Protein Res.* 36:544–550, Munksgaard (1990).

Tyagi, S.C. and Carter, C.A., "Continuous Assay of the Hydrolytic Activity of Human Immunodeficiency Virus–1 Protease," *Anal. Biochem.* 200:143–148, Academic Press, Inc. (1992).

Weber, J.M., "Adenovirus Endopeptidase and Its Role in Virus Infection," in: The Molecular Repetoire of Adenoviruses I. Virion Structure and Infection, Doerfler, W. and Böhm, eds., Springer–Verlag, Berlin, Germany, pp. 227–235 (1995).

Zhang, R., et al., "Probing and Substrate Specificity of Hepatitis C Virus NS3 Serine Protease by Using Synthetic Peptides," *J. Virol.* 71:6208–6213, American Society for Microbiology (1997).

Allen, R.T., et al., "Mechanisms controlling cellular suicide: role of Bcl–2 and caspases," *Cell. Mol. Life Sci.* 54:427–445, Birkhäuser Verlag (1998).

* cited by examiner

MICE: C3H/HeN
ADMINISTRATION: INTRAPERITONEALLY ADMINISTERED 1hr BEFORE ConA INJECTION
Con A: 0.5 mg/MOUSE I.V.
COLLECTION OF BLOOD: 24hrs AFTER Con A INJECTION

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Fluorogenic substrate
<221> NAME/KEY: MOD_RES
<222> LOCATION: (1)..(1)
<223> OTHER INFORMATION: ACETYLATION

<400> SEQUENCE: 1

Asp Glu Val Asp
1
```

METHOD OF IDENTIFYING IMMUNOSUPPRESSIVE AGENTS

CROSS REFERENCE TO RELATED APPLICATIONS

This application claims the benefit of U.S. Provisional Application No. 60/222,897, filed Aug. 3, 2000.

BACKGROUND OF THE INVENTION

1. Field of the Invention

This invention is in the field of assays useful for the screening of chemical compounds able to serve as immunosuppressive agents.

The present invention arises from the discovery of a method for the identification of agents that selectively induce apoptosis in activated T lymphocytes. Compounds of this nature are useful as therapeutically effective immunosuppressive agents. In particular, the invention relates to the use of primary T cell cultures to identify compounds that directly or indirectly activate the caspase cascade.

Also taught are methods for using the immunosuppressive agents and pharmaceutical compositions for their use.

2. Related Art

Immunopathological Diseases: The immune system is a remarkably evolved defense system in vertebrates for protection against pathogenic microorganisms. The same immune system can also lead to various pathological conditions. For example, the immune system can cause rejection of grafts during transplantation (Rosenberg, A. and S. Singer, *Annu. Rev. Immunol.* 10:333 (1992)). Also, graft versus host disease (GvHD) develops when a graft containing immunocompetent T cells recognize and react with the recipient's cells (Woo, S.-B., et al., *Crit. Rev. Oral. Biol. Med.* 8:201 (1997)). Mechanisms of self-tolerance normally protect an individual from self-reactive T lymphocytes. However, should these mechanisms fail, an inappropriate immune response occurs leading to what is known as autoimmunity. Rheumatoid arthritis is a well-known example of autoimmunity. In this degenerative condition, auto-reactive T cells destroy the tissue around the joints causing inflammation and tissue destruction.

Transplantation or Graft Rejection: A problem arises during kidney, cardiac, lung or liver transplants and skin grafts when the host immune system recognizes the transplant graft as foreign tissue and develops immune reactivity that ends in rejection of the transplanted/grafted tissue. Several attempts are being made to induce immunological tolerance across the major histocompatibility complex (MHC) barriers. This is generally achieved by three mechanisms:

1) clonal deletion of the activated antigen/MHC reactive lymphocytes:

2) clonal anergy and suppression on the other hand by antibody mediated blockade of the gene expression; or 3) Suppression of one subset of the T cells (Th1) and expansion of the other (Th2) in situations of cardiac allografts studies were also partly successful (Bach. F., et al., *Nat. Med.* 3:196–204 (1997); Sayegh, M H., et al., *J. Exp. Med.* 181:1869–1874 (1995).

Graft-Versus-Host Disease (GvHD): GvHD is the most important complication of bone marrow transplantation (BMT) (Ferrara, J. and H. Deeg, *N. Engl. J. Med.* 324:667 (1991)). When competent T cells are transferred from a donor to a recipient who is incapable of rejecting them, the grafted cells survive, start recognizing the host antigens and develop immune reactivity towards them. Instead of the normal transplantation reaction of host versus graft, the reverse is seen in this case. Research indicates that increased donor T cell and monocyte/macrophage expansion and inflammatory cytokines are responsible for this syndrome (Via, C., et al, *J. Immunol.* 157:5387 (1996): Krenger, W., et al, *Transplantation* 64:553 (1997); Hattori, K., et al., *Blood* 91:4051 (1998); Mori, T., et al., *Blood* 92:101 (1998)).

Autoimmune Diseases: Among this group of diseases is rheumatoid arthritis which is a chronic inflammatory disease of the joints, characterized by infiltration of T lymphocytes into the synovial fluid and eventual destruction of the cartilage and bones in the affected joints. Several studies have suggested that the infiltrating T lymphocytes are activated and cause neighboring tissue destruction. Other autoimmune diseases due to autoreactive T lymphocytes include multiple sclerosis, insulin-dependent diabetes mellitus, lupus, and muscular dystrophy (Liblau, R., et al., *Immunol. Today* 16:34 (1995)).

Immunosuppressive Agents: Current immunosuppressive treatments result in generalized immunosuppression and leave the patient prone to various infections. These therapies are also aimed at slowing down the proliferation of activated T cells and thereby due to lack of specificity, effect the growth of all normal dividing cells and result in side effects and toxicity. The primary methods of treatment for immunopathological disorders such as graft or transplantation rejection. GvHD and rheumatoid arthritis are corticosteroid and immunosuppressive agents. Current immunosuppressive drugs like cyclosporin A (CsA) and FK506 work by blocking a calcium dependent protein phosphatase calcineurin (Cn), but they often have unwanted side effects such as cancer, kidney failure, and diabetes. Progress is being made in enhancing the effectiveness of each of these agents.

Despite reduced side effects from immunosuppression, certain tissue transplantations still result in morbidity and mortality. Because of the frequent occurrence of corticosteroid related side effects in transplant patients, alternative therapeutic agents are desirable for these and other related disorders. One such therapeutic agent is methotrexate (MTX), a folate antagonist first developed for malignancies (Farber, S., et al., *Advances in Cancer Res.* 2–73 (1956)) and subsequently used as an anti-inflammatory and/or immunosuppressive drug. MTX is now the most commonly used treatment for rheumatoid arthritis (Weinblatt, M., et al., *N. Engl. J. Med.* 312:818–822(1985); Williams, B., et al., *Arthritis Rheum.* 28:721–730 (1985)).

Apoptosis: A normal checkpoint in the life of cells in multicellular organisms is the process of apoptosis (see, e.g., Evan and Littlewood, *Science* 281:1317–1322 (1998)). Apoptosis is the highly conserved mechanism by which cells commit suicide. Characteristics of the process include an execution phase that includes loss of cell volume, plasma membrane blebbing and chromatin condensation, followed by packing of the cellular contents into membrane-enclosed vesicles called apoptotic bodies that are rapidly phagocytosed by neighboring cells. Apoptosis differs from necrosis, which is cell death resulting from physical injury.

Since autoimmune diseases and certain degenerative diseases also involve the proliferation of abnormal cells, therapeutic treatment for these diseases could also involve the enhancement of the apoptotic process through the administration of appropriate drugs.

It is pertinent, therefore, to inquire into the mechanism of apoptosis in order to develop a method for the identification of compounds for the treatment of autoimmune diseases. It has been found that a group of proteases are a key element in apoptosis (see e.g. Thornberry, *Chemistry and Biology* 5:R97–R103 (1998); Thornberry, *British Med. Bull.* 53:478–490 (1996)). Genetic studies in the nematode *Caenorhabditis elegans* revealed that apoptotic cell death involves at least 14 genes, two of which are the pro-apoptotic (death-promoting) ced (for cell death abnormal) genes, ced-3 and ced-4. CED-3 is homologous to interleukin 1β-converting enzyme (ICE), a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 10 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

The caspase cascade can be involved in disease processes in two major aspects. Excessive activity of the caspase cascade can lead to excessive apoptosis and organ failure. Among the diseases that could result from this excessive activity are myocardial infarction, congestive heart failure, viral infections, rheumatoid arthritis and others. Inhibitors of the caspase cascade could thus be candidates for therapeutic intervention in such diseases.

Caspase Cascade Activators: Although the development of enzyme inhibitors as therapeutic agents is a well-understood art (see Muscate and Kenyon, *Burger's Medicinal Chemistry* 1:733–782, 5$^{th}$ Ed. (1995)) this is not the case in the development of enzyme activators. The theoretical basis for the development of enzyme activators is still in its infancy. In the case of the apoptosis process, control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see Schmitt, et al. *Biochem. Cell. Biol.* 75:301–314 (1997)). BCL-like proteins include BCL-xL and BAX-α, which appear to function upstream of caspase activation. BCL-xL appears to prevent activation of the apoptotic protease cascade, whereas BAX-α accelerates activation of the apoptotic protease cascade. Although the exact mechanisms are not fully understood, it is clear that the possibility exists for the activation of the caspase cascade. Because insufficient activity of the caspase cascade and consequent apoptotic events appear to be implicated in various types of immunopathological, degenerative and autoimmune diseases, the development of caspase cascade activators is a highly desirable goal in the development of potentially therapeutically effective immunosuppressive agents.

Assays for Detecting Caspase Cascade Activating Drugs: In order to find drugs that either inhibit or stimulate the caspase cascade, it is necessary to develop high-throughput caspase activation (HTCA) assays. These HTCA assays must be able to monitor activation or inhibition of the caspase cascade inside living cells. Ideally, HTCA assays should be versatile enough to measure the caspase cascade activity inside any living cell, no matter what its origin might be: cancer cells, tumor cells, immune cells, brain cells, cells of the endocrine system, cells or cell lines from different organ systems, biopsy samples, etc. Furthermore, such HTCA assays should be able to measure within living cells the activation or inhibition of any of the caspase enzymes or any other enzymes that are involved in the caspase cascade. Developing such versatile HTCA assays represents a substantial advance in the field of drug screening.

Most HTCA assays do not permit intracellular screening for compounds that can either activate or inhibit the caspase cascade. These assays are typically cell-free, high-throughput screening assays to measure the activity of individually isolated caspase enzymes, or assays that can measure the activity of caspases in dead cells which have been permeabilized by osmotic shock (see Los, et al., *Blood,* 90:3118–3129 (1997)). But these enzyme assays cannot predict the effect of a compound on the caspase cascade in living cells for the following reasons:

1) Cell free assays, or assays using dead, permeabilized cells, cannot predict the ability of compounds to penetrate the cellular membrane. This is crucial because the caspase cascade resides in the interior of the cells. In order to be active, a compound must not only be able to modulate the caspase enzyme or enzymes, but it must also be able to penetrate the intact cell membrane. Cell-free assays or assays using dead cells are therefore unable to determine whether or not a compound will be potentially useful as a drug.

2) Isolated caspases in cell-free assays are highly susceptible to oxidation and to compounds that can cause oxidation of the enzymes. This property of isolated caspases makes cell free caspase screening assays highly susceptible to artifacts and has precluded successful use of these assays for high-throughput screening of combinatorial (or other) chemical libraries. Previous mass screening efforts, using cell-free caspase enzyme assays, have led to discovery of numerous inhibitors which oxidize caspases, but no compound that would be useful as a potential drug. Others have reported similar difficulties.

3) Numerous cellular receptors, proteins, cell constituents and cofactors—many of which are still unknown—can influence the caspase cascade in living cells. Cell-free caspase assays or assays using permeabilized, dead cells do not take into account these cellular receptors and cofactors. Because of this, it is possible that a compound identified in a cell-free or dead-cell caspase assay will not work in living cells. On the other hand, a compound that might inhibit or stimulate the caspase cascade indirectly through one of the cellular receptors or cofactors would be missed entirely in a cell-free or dead-cell caspase assay.

4) It is highly likely that the caspase cascade functions differently in cells derived from different organs. There is growing evidence that the receptors and cofactors that influence the caspase cascade differ among cell types. Using cell-free or dead cell assays, it would be virtually impossible to identify cell-type or organ specific modulators of the caspase cascade.

U.S. Pat. No. 6,077,684 discloses a method of measuring the apoptosis-inducing activity of a substance using cultured, isolated cells having intact membranes. This method involves obtaining a sample of cells from a subject; isolating a single cell suspension from the sample; placing the cells in culture conditions; exposing the cells in culture to the putative apoptosis-inducing substance; incubating the cultured cells; measuring in a serial manner the optical densities of the culture to obtain an optical density curve; and correlating the slope of a line representing an increase over time in optical density, due to cellular membrane distortion and blebbing, with an increase in apoptotic activity.

U.S. Pat. No. 6,342,611 and WO 99/18856 disclose a whole cell assay wherein a fluorogenic or fluorescent reporter compound is used to measure the activity of intracellular caspases or other enzymes involved in apoptosis in living or dead whole cells or tissues. In this process, test substances, which may directly or indirectly induce apoptosis, are brought into contact with cells having intact membranes. If one or more of the substances is capable of inducing apoptosis, then intracellular caspase proteases are generated. The reporter compound serves as a substrate for these proteases and fluoresces after being cleaved. The reporter molecules can also be used to measure baseline caspase activity in cells that are not undergoing induced apoptosis. Hence, apoptosis inducing agents may be discovered by monitoring changes in fluorescence occurring within the cells. This process may be used to find new compounds or new uses for known compounds in reducing, preventing or treating maladies in which apoptotic cell death is either a causative factor or a result.

BRIEF SUMMARY OF THE INVENTION

The present invention is directed to methods for identifying direct and indirect activators of the caspase cascade in T cells, therapeutic methods employing such activators, compositions comprising such activators, and kits comprising such activators.

In particular, the invention provides a method for identifying immunosuppressive compounds by determining the ability of test compounds to selectively activate the caspase cascade in activated, viable T cells to a greater extent than in resting viable T cells. Test compounds which are capable of acting outside of the cell, at the cellular membrane, or within the cell to directly or indirectly induce the caspase cascade may be identified due to the presence of intracellular proteases generated as a result of the caspase cascade. Such proteases cleave a reporter molecule which serves as a substrate of the proteases.

More particularly, the invention relates to a method for identifying an immunosuppressive agent comprising obtaining at least one population of viable cultured active T cells having intact cell membranes from a cell growth medium under conditions conducive to growth; combining a first portion of the at least one population with a predetermined amount of at least one test compound dissolved in a solvent for a predetermined period of time at a predetermined temperature thereby generating a first volume; combining a second portion of the at least one population with an amount of the solvent which was used to dissolve the at least one test compound, for the predetermined period of time at the predetermined temperature thereby generating a second volume; separately adding to each of the first volume and the second volume a reporter compound having at least one measurable property which is responsive to the caspase cascade; measuring the at least one measurable property of the reporter compound in the first volume and thereby measuring the caspase cascade activity of the first volume; measuring the at least one measurable property of the reporter compound in the second volume and thereby measuring the caspase cascade activity of the second volume; calculating a first ratio of caspase cascade activity measured for the first volume to the caspase cascade activity measured for the second volume, wherein when the first ratio is greater than one, the at least one test compound kills T cells and is identified as a potential immunosuppressive agent.

Subsequent to identifying a potential immunosuppressive agent, the invention comprises obtaining at least one population of viable cultured resting T cells having intact cell membranes from a cell growth medium under conditions conducive to growth; combining the resting T cells with the predetermined amount of the identified immunosuppressive agent dissolved in the solvent for the predetermined period of time at the predetermined temperature thereby generating a third volume; adding to the third volume the reporter compound having at least one measurable property which is responsive to the caspase cascade; measuring the at least one measurable property of the reporter compound in the third volume and thereby measuring the caspase cascade activity of the third volume; and, calculating a second ratio of caspase cascade activity measured for the first volume to the caspase cascade activity measured for the third volume, wherein when the second ratio is greater than one, then the identified immunosuppressive agent is further identified as an active-T-cell-selective immunosuppressive agent.

The invention also relates to a method for identifying an immunosuppressive agent comprising obtaining at least one population of viable cultured active T cells having intact cell membranes from a cell growth medium under conditions conducive to growth; combining a first portion of the at least one population with a predetermined amount of at least one test compound dissolved in a solvent for a predetermined period of time at a predetermined temperature thereby generating a first volume; combining a second portion of the at least one population with an amount of the solvent which was used to dissolve the at least one test compound, for the predetermined period of time at the predetermined temperature thereby generating a second volume; separately assessing the cell viability of the first volume and the second volume; and comparing the cell viability of the first volume to the cell viability of the second volume, wherein when the cell viability of the first volume is less than the cell viability of the second volume, the at least one test compound kills T cells and is identified as a potential immunosuppressive agent.

Subsequent to identifying a potential immunosuppressive agent, the invention relates to a method of obtaining at least one population of viable cultured resting T cells having intact cell membranes from a cell growth medium under conditions conducive to growth; combining the resting T cells with the predetermined amount of the identified immunosuppressive agent dissolved in the solvent for the predetermined period of time at the predetermined temperature thereby generating a third volume; assessing the cell viability of the third volume; and comparing the cell viability of the first volume to the cell viability of the second volume, wherein when the cell viability of the first volume is less than the cell viability of the second volume, then the identified immunosuppressive agent is further identified as an active-T-cell-selective immunosuppressive agent. Cell viability may be assessed by observing mitochondrial activity, membrane intactness, or cell number. Mitochondrial activity, membrane intactness, or cell number may be measured by using fluorescence methodology, calorimetric assays, or direct visualization techniques, and by using a reporter compound selected from the group consisting of a fluorogenic compound that produces fluorescence under the influence changes in mitochondrial activity, membrane intactness, or cell number; a chromogenic compound that produces light absorption under the influence of changes in mitochondrial activity, membrane intactness, or cell number; and a chemiluminescent compound that produces light emission under the influence of changes in mitochondrial activity, membrane intactness, or cell number.

The invention also relates to a method for assaying the potency of a test compound to synergise with a known immunosuppressant by functioning as an activator of the caspase cascade, comprising obtaining at least one population of viable cultured active T cells having intact cells by culturing T cells in a cell growth medium under conditions conducive to growth and activating the cells; exposing a first portion of the at least one population to a combination of a predetermined amount of the test compound and a subinducing amount of the known immunosuppressant for a first predetermined period of time, at a first predetermined temperature thereby generating a first volume; exposing a second portion of the at least one population to an amount of solvent which was used to dissolve the test compound and to the subinducing amount of the known immunosuppressant for the first predetermined period of time at the first predetermined temperature thereby generating a second volume; adding a reporter compound to the first volume and to the second volume, the reporter compound having at least one measurable property which is responsive to the caspase cascade; incubating the resulting mixture of the first volume with the reporter compound for a second predetermined time period at a second predetermined temperature; incubating the resulting mixture of the second volume with the reporter compound for the second predetermined time period at the second predetermined temperature; measuring the at least one measurable property of the reporter compound in each of the resulting mixtures and thereby measuring the caspase cascade activity of the first volume and of the second volume; and, calculating the ratio of measured caspase cascade activities of the first volume to the second volume to determine whether the test compound synergises with the known immunosuppressant as an activator of the caspase cascade.

The invention also relates to a method for identifying an immunosuppressive agent by determining the ability of at least one test compound to activate the caspase cascade in active T cells having intact cell membranes, comprising obtaining viable cultured active T cells having an intact cell membrane; obtaining viable cultured resting T cells having an intact cell membrane; separately exposing the active and resting T cells to at least one test compound for a predetermined period of time under predetermined conditions; adding a reporter compound having at least one measurable property which is responsive to the caspase cascade to the active and resting T cells; and measuring the caspase cascade activity in the active T cells by measuring the at least one measurable property; measuring the caspase cascade activity in the resting T cells by measuring the at least one measurable property; wherein when the caspase cascade activity in the active cells is greater than the caspase cascade activity in the resting cells, the at least one test compound selectively kills active T cells and is an immunosuppressive agent.

BRIEF DESCRIPTION OF THE DRAWINGS/ FIGURES

DETAILED DESCRIPTION OF THE PREFERRED EMBODIMENTS

Figure 1:
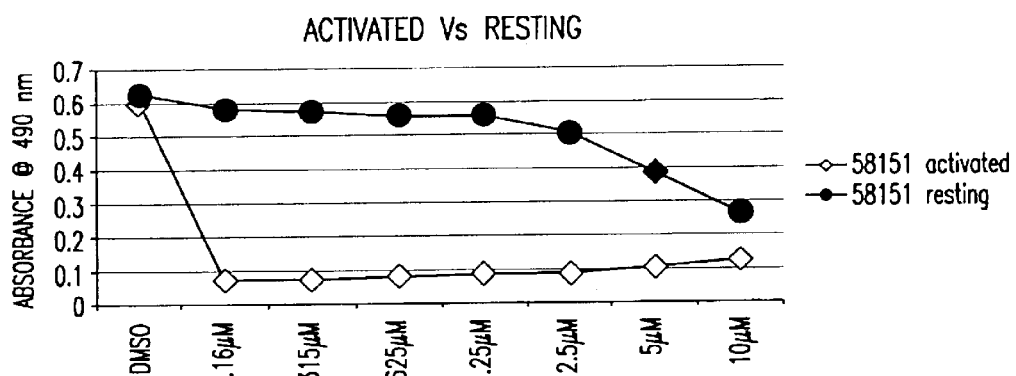
FIG. 1 depicts a graph showing the absorbance of a reporter molecule, of mitochondrial activity, as a function of various concentrations of test compound 2-amino-3-cyano-7-dimethylamino-4-(3-bromo-4,5-dimethoxyphenyl)-4H-chromene (CV58151) in activated (diamonds) and resting (filled circles) T cells.

Definitions: Unless defined otherwise, all technical and scientific terms used herein have the same meaning as is commonly understood by one of ordinary skill in the art to which this invention belongs.

As used herein, apoptosis is a highly conserved, genetically programmed form of cellular suicide characterized by distinct morphological changes such as cytoskeletal disruption, cell shrinkage, membrane blebbing, nuclear condensation, fragmentation of DNA, and loss of mitochondrial function.

As used herein, a caspase is a cysteine protease of the interleukin-1β CED-3 family. As used herein, the caspase cascade is a sequential activation of at least two caspases, or the activation of caspase activity that behaves as if it involves the sequential activation of at least two caspases.

As used herein, T cell is interchangeable with T lymphocyte.

As used herein, an active T cell is a mature T cell which has encountered antigen and has differentiated into an effector lymphocyte with functions in protective immune responses, and a resting T cell is a mature T cell that has not encountered antigen to become an effector lymphocyte. Such active T cells may be obtained according to methods known in the art and the methods described herein.

As used herein an effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the disease. Typically, repeated administration is required to achieve the desired amelioration of symptoms.

As used herein, an activator of the caspase cascade is a compound, such as a drug or antibody, that enhances caspase-mediated physiological responses such as cellular apoptosis. The activator may act by any one or a combination of mechanisms.

As used herein, pharmaceutically acceptable salts or prodrugs of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxyl groups can be esterified (e.g., with a $C_{2\text{-}10}$ alkanoyl group or succinic acid) or etherified (with a $C_{1-6}$ alkoxy methylchloride). In addition, a carboxylic acid group may be esterified (e.g. with a $C_{1-6}$ alcohol). Examples of such salts include the acid addition salts of amino compounds. Such salts include the chloride, sulfate, hemisulfate, phosphate, hydrogen phosphate, dihydrogen phosphate, acetate, maleate, succinate, and the like. Other salts include the salts of carboxy-containing compounds which may be prepared by reacting the carboxy-containing compound with a base such as sodium hydroxide, lithium hydroxide, potassium hydroxide, sodium bicarbonate, sodium carbonate, and the like.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady, *Medicinal Chemistry: A Biochemical Approach*, Oxford University Press, New York, pages 388–392 (1985)). For example, succinylsulfathiazole is a prodrug of 4-amino-N-(2-thiazoyl) benzenesulfonamide (sulfathiazole) that exhibits altered transport characteristics.

As used herein, treatment means any manner in which the symptoms of a condition, disorder or disease are ameliorated or otherwise beneficially altered.

Animals which may be treated according to the present invention include all animals which may benefit from the administration of an immunosuppressive agent identified according to the present invention. Such animals include mammals such as humans, cows, pigs, sheep, dogs, cats, horses, and the like.

As used herein, amelioration of the symptoms of a particular disorder by administration of a particular pharmaceutical composition refers to any lessening, whether permanent or temporary, lasting or transient, that can be attributed to or associated with administration of the composition.

As used herein, substantially pure means sufficiently homogeneous to appear free of readily detectable impurities as determined by standard methods of analysis such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound, however, may be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions, and mixtures.

As used herein, a fluorogenic, chromogenic or chemiluminescent substrate is a substance that produces fluorescence, light absorption within the ultraviolet, visible or infrared spectrum, or light emission under the influence of the caspase cascade.

Identifying Compounds That Activate the Caspase Cascade: The test compounds may be pure substances or mixtures of substances such as in combinatorial libraries. The test compounds may be any natural product, synthesized organic or inorganic molecule, or biological macromolecules.

The reporter molecule is composed of at least two covalently linked parts. One part is an amino acid sequence, which may be recognized by any of the intracellular proteases or peptidases that are produced as a result of caspase cascade activation. This sequence is bonded to an aromatic or conjugated moiety that undergoes a detectable physical change upon its release from all or part of the amino acid sequence. Such moieties include a fluorogenic moiety that fluoresces more strongly after the reporter molecule is hydrolyzed by one of the proteases, a chromogenic moiety that changes its light absorption characteristics after the reporter molecule is hydrolyzed by one of the proteases, or a chemiluminescent moiety that produces light emission after the reporter molecule is hydrolyzed by one of the proteases. Alternatively, the aromatic or conjugated moiety may be linked to a plurality of amino acid sequences.

One type of such a reporter molecule is given by Formula I:

x-y-z    (I)

or biologically acceptable salts or pro-reporter molecules (such as methyl ester form of carboxyl-containing amino acid residues) thereof, wherein x and z is the same or different and is a peptide or amino acid or acyl group or other structure such that compounds of Formula I are substrates for a caspase or other enzyme involved in the intracellular apoptosis cascade; and wherein the scissile bond is only one or both of the x-y and y-z bonds in Formula I when x is the same as z, or wherein the scissile bond is only one of the x-y or y-z bond in Formula I when x is not the same as z, y is a fluorogenic or fluorescent moiety.

Preferred compounds are represented by Formula II:

$R_1$-(AA)$_n$-Asp-y-Asp-(AA)$_n$-$R_1$    (II)

or biologically acceptable salts or pro-reporter molecules (such as methyl ester form of carboxyl-containing amino acid residues) thereof, wherein $R_1$ is an N-terminal protecting group such as t-butyloxycarbonyl, acetyl, and benzyloxycarbonyl; each AA independently is a residue of any natural or non-natural α-amino acid or β-amino acid, or derivatives of an α-amino acid or β-amino acid; each n is independently 0–5; and y is a fluorogenic or fluorescent moiety. Preferred y is a Rhodamine including Rhodamine 110, Rhodamine 116 and Rhodamine 19. Most preferred y is Rhodamine 110.

Especially preferred compounds are represented by Formula III:

(III)

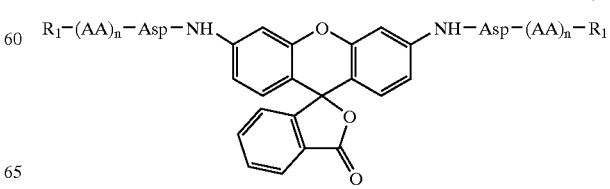

or biologically acceptable salts or pro-reporter molecules (such as methyl ester form of carboxyl-containing amino acid residues) thereof, wherein $R_1$, AA, n are as defined previously in Formula II. Preferred $R_1$ is t-butyloxycarbonyl, acetyl and benzyloxycarbonyl. Preferred values of n are 1–3.

Another group of preferred compounds falling within the scope of Formula I include compounds wherein x is not the same as z. Preferred compounds of this group include those wherein x is a peptide or other structure which makes the compound a substrate for a caspase or other enzyme related to apoptosis, and the x-y bond in Formula I is the only bond which is scissile under biological conditions. z is a blocking group and the y-z bond in Formula I is not a scissile bond under biological conditions.

Specifically, the fluorogenic or fluorescent reporter compounds that may be used in this invention are of Formula V:

$$R_1\text{-}(AA)_n\text{-}Asp\text{-}y\text{-}R_6 \qquad (V)$$

or biologically acceptable salts or pro-reporter molecules (such as methyl ester form of carboxyl-containing amino acid residues) thereof, wherein:

$R_1$, AA, n and y are as defined previously in Formula II; and $R_6$ is a blocking group which is not an amino acid or a derivative of an amino acid.

Preferred $R_6$ blocking groups include, but are not limited to, an alkyloxycarbonyl group such as methoxycarbonyl, an arylalkyloxycarbonyl group such as benzyloxycarbonyl, a $C_{2-6}$ acyl (alkanoyl) group such as acetyl, a carbamyl group such as dimethylcarbamyl, and an alkyl, haloalkyl or aralkyl sulfonyl group such as methanesulfonyl. Preferred y is a Rhodamine including Rhodamine 110, Rhodamine 116 and Rhodamine 19. Most preferred y is Rhodamine 110.

In particular, preferred embodiments of the compounds of Formula V are represented by Formula VII:

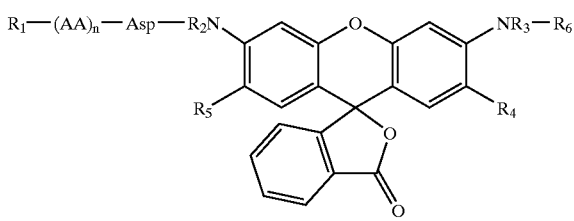

(VII)

or biologically acceptable salts or pro-reporter molecules (such as methyl ester form of carboxyl-containing amino acid residues) thereof, wherein:

$R_1$, $R_6$, AA and n are as defined previously in Formulae II and V;

$R_2$ and $R_3$ are the same or different and are independently hydrogen, alkyl or aryl; and $R_4$ and $R_5$ are the same or different and are independently hydrogen or alkyl.

Preferred $R_1$ is t-butyloxycarbonyl, acetyl and benzyloxycarbonyl. Preferred n is 1–3. Preferred $R_2$ and $R_3$ are hydrogen, methyl or ethyl. Preferred $R_4$ and $R_5$ are hydrogen or methyl. Preferred $R_6$ blocking groups include, but are not limited to, an alkyloxycarbonyl group such as methoxycarbonyl, an arylalkyloxycarbonyl group such as benzyloxycarbonyl, an acyl group such as acetyl, a carbamyl group such as dimethylcarbamyl, and an alkyl, haloalkyl or aralkyl sulfonyl group such as methanesulfonyl.

Other fluorogenic substrates useful in the practice of the present invention are disclosed in the following U.S. Pat. Nos. 4,336,186; 4,557,862; 4,640,893; 5,208,148; 5,227,487; 5,362,628; 5,443,986; 5,556,992; 5,587,490; 5,605,809; 5,698,411; 5,714,342; 5,733,719; 5,776,720, 5,849,513; 5,871,946; 5,897,992; 5,908,750; 5,976,822. Useful or related substrates are also described in EP 0285179 B1; EP 623599 A1; WO 93/04192; WO 93/10461; WO 96/20721; WO 96/36729; WO 98/57664; Ganesh, S. et al., *Cytometry* 20:334–340 (1995); Haugland, R. and Johnson, I., *J. Fluorescence* 3:119–127 (1993); Haugland, R., *Biotechnic and Histochemistry* 70:243–251 (1995); Haugland. R., Molecular Probes Handbook of Fluorescent Probes and Research Chemicals, pp. 28 and 54, 6th Ed. (1996); Holskin, B., et al., *Anal. Biochem.* 226:148–155 (1995); Johnson, A., et al., *Anal. Chem.* 65:2352–2359 (1993); Klingel, S., et al., *Methods in Cell Biology* 41:449–459 (1994); Leytus, S., et al., *Biochem. J* 215:253–260 (1983); Leytus, S., et al., *Biochem. J.* 209:299–307 (1983); Matayoshi, E., et al., *Science* 247:954–958 (1990); Morliere, P., et al., *Biochem. Biophys. Res. Commun.* 146:107–113 (1987); O'Boyle, D., et al., *Virology* 236:338–347 (1997); Richards, A., et al., *J. Biol. Chem.* 265:7733–7736 (1990); Rothe, G., et al., *Biol. Chem. Hoppe-Seyler* 373:547–554 (1992): Stevens. J., et al., *Eur J Biochem.* 226:361–367 (1994); Tamburini, P., et al, *Anal Biochem.* 186:363–368 (1990); Thornberry, N., et al, *J Biol Chem* 272:17907–17911 (1997); Toth, M. and Marshall, G., *Int. J. Peptide Protein Res* 36:544–550 (1990): Tyagi, S. and Carter, C., *Anal. Biochem.* 200:143–148 (1992); Weber, J. "Adenovirus Endopeptidase and Its Role in Virus Infection" in The Molecular Repertoir of Adenoviruses I, Doerfler, W. and Bohm, P. eds., pp. 227–235, Springer Press, New York (1995); Zhang, R., et al., *J. Virology* 71:6208–6213 (1997); Mangel, W., et al., *Biol. Chem. Hoppe-Seyler* 373:433–440 (1992); Bonneau, P., et al., *Anal. Biochem.* 255:59–65 (1998); and DiIanni, C., et al., *J. Biol. Chem.* 268:25449–25454 (1993).

Immune system cells may be prepared for testing from peripheral blood lymphocytes (PBMC) obtained from humans or other mammals (Roitt, I., Essential Immunology 1988). PBMC from eukaryotic origin may be enriched in T lymphocytes by a process of leukapheresis and density gradient centrifugation. Such lymphocyte preparations contain few monocytes and no B lymphocytes or Dendritic cells. The enriched T cells may be activated e.g. with antibodies to the T cell receptor, or with the lectins Concanavalin A (ConA) or Phytohaemagglutinin (PHA). Cells may be activated for various lengths of time (e.g., from 0 to 6 days) and then treated with the testing compounds for different lengths of time. A plurality of viable cultured active and resting T cells may be tested in separate wells of a microtiter plate.

Alternatively, immune system cells may be cultured and purified directly from collected patient tissue samples. In such preparations, active T cells may be cultured and purified from tissue afflicted with one or more immunopathological symptoms. Resting T cells may be cultured and purified from healthy tissue that is not afflicted with any immunopathological symptoms. The resting T cells may be obtained from the same or a different patient. Both the active and resting T cells may then be treated with the testing compounds according to the methods described herein.

A caspase substrate reporter molecule is used to determine caspase activation and apoptosis in the cells. However, inasmuch as the caspase cascade takes place in the intracellular environment, measures may be undertaken to enhance transfer of the reporter compound across the cell membrane. This can be accomplished with a suitable permeabilization agent. Preferable permeabilization agents include but are not limited to, NP-40, n-octyl-O-D-glucopyranoside, n-octyl-O-D-thioglucopyranoside, taurocholic acid, digitonin, CHAPS, lysolecithin, dimethyldecylphosphine oxide (APO-10), dimethyldodecylphosphine oxide (APO-12), N,N-bis-(3-D-gluconamidopropyl) cholamide (Big Chap), N,N-bis-(3-D-gluconamidopropyl) deoxycholamide (Big Chap, deoxy), BRIG-35, hexaethyleneglycol (C10E6), C10E8, C12E6, C12E8, C12E9, cyclohexyl-n-ethyl-O-D-malt cyclohexyl-n-hexyl-O-D-maltoside, cyclohexyl-n-methyl-O-D-maltoside, polyethylene glycol lauryl ether (Genapol C-100), polyethylene glycol dodecyl ether (Genapol X-80), polyoxyethylene isotridecyl ether (Genapol X-100), n-decanoylsucrose, n-decyl-O-D-glucopyranoside, n-decyl-O-D-maltopyranoside, n-decyl-O-D-thiomaltoside, n-dodecanoylsucrose, n-dodecyl-O-D-glucopyranoside, n-dodecyl-O-D-maltoside, n-heptyl-O-D-glucopyranoside, n-heptyl-O-D-thioglucopyranoside, n-hexyl-O-D-glucopyranoside, n-nonyl-O-D-glucopyranoside, n-octanoylsucrose, n-octyl-O-D-maltopyranoside, n-undecyl-O-D-maltoside, n-octanoyl-O-D-glucosylamine (NOGA), PLURONIC® F-127, PLURONIC® F-68, and dimethyl sulfoxide (DMSO).

Preferably, a reporter compound for measuring caspase activity with or without a permeabilization enhancer is added to the cell after the test compound has been incubated with the cell for a predetermined time to allow transport of the test compound across the cell membrane or interaction of the test compound with receptors on the surface of the cell membrane. The predetermined period of time may be about 1 minute to about 48 hours, preferably about 1–24 hours, and most preferably about 3, 5, or 24 hours. The predetermined temperature may be about 4° C. to about 42° C., preferably about 37° C.

The predetermined period of time used in the present invention is sufficiently short to maintain an intact cell membrane in the cells being used in the assay, and makes possible the specificity of the present method for activators of the caspase cascade that are immunosuppressive agents, rather than nonspecific cell poisons. The intactness of the cell membrane may be confirmed by use of propidium iodide (available from Aldrich Chemical Co.). Tested agents found to be active may be confirmed and tested for specificity by testing with various dividing and resting cell types of different tissue or organ origin. This testing results in the identification of compounds that are not active or are less active in inducing apoptosis in resting T cells or in cells other than T cells. Compounds that possess such selectivity are useful as immunosuppressive agents.

Such compounds are useful for treating, preventing or ameliorating immune-mediated injuries or immunopathological disorders such as ankylosing spondylitis, reactive arthritis, undifferentiated spondyloarthropathy, Behcet's syndrome, dermatomyositis/polymyositis, immediate type hypersensitivity, nephropathies, rheumatoid arthritis, sarcoidosis, Sjogren's syndrome, skin diseases, systemic lupus erythematosus, systemic sclerosis, immune-mediated injuries from transfusions, vasculitis syndromes, graft rejection, graft versus host disease, multiple sclerosis, endocrine ophthalmopathy, uveoretinitis, the autoimmune phase of Type 1 diabetes, myasthenia gravis, Grave's disease, glomerulonephritis, autoimmune hepatological disorder, autoimmune inflammatory bowel disease, Crohn's disease, and inflammation having immune reaction characteristics such as anaphylaxis or allergic reaction.

Measuring the Potency of Caspase Cascade Activation: Using a fluorescent plate reader, an initial reading (T=0) is made immediately after addition of the reporter reagent solution, employing excitation and emission at an appropriate wavelength (preferably excitation at 485 nm and emission at 530 nm) to determine the background absorption and/or fluorescence of the control sample. After the incubation, the absorption and/or fluorescence of the sample is measured as above (e.g., at T=1 hr).

Sample Calculation: Measured relative fluorescence unit (RFU) values are used to calculate the potency of the test compounds. Equation (1) affords determination of the time dependent change in fluorescence of active or resting T Cells both in the presence and absence of some test compound:

$$RFU_{(T=1\ hr)} - RFU_{(T=0)} = \text{Net RFU} \quad (1)$$

If some particular test compound serves directly or indirectly as a caspase cascade activator (i.e. induces apoptosis), then the apoptosis proteases present will cleave the fluorescent substrate resulting in an increase in fluorescence.

By use of equation (1), a comparison of how a particular test compound effects active T cells relative to resting T cells is easily made. When the caspase cascade activity (caused by the particular test compound) in the active T cells is greater than the caspase cascade activity in the resting cells, then the test compound selectively kills active T cells and is expected to be an effective immunosuppressive agent.

Determining the efficacy of an immunosuppressive agent that selectively kills active T cells may be accomplished by using the following ratio:

$$\frac{\text{Net RFU of test compound}}{\text{Net RFU of control sample}} = \text{Ratio} \quad (2)$$

where the numerator represents the Net RFU observed when the active T cells are in the presence of the immunosuppressive agent; and, the denominator represents the NET RFU observed when none of the immunosuppressive agent is present in the active T cells. Preferred test compounds are those indicating a ratio of 2.0 or greater and most preferably with a measured ratio greater than a statistically significant value calculated as:

$$(\text{Average Control RFU} + (4 \times SD_{control})) / (\text{Avereage Control RFU}) \quad (3)$$

wherein SD refers to the standard deviation.

Equation (2) may also be used to determine the ability of a known immunosuppressant to synergise with a test compound in order to activate the caspase cascade. In this scenario, the numerator represents the observable NET RFU in the active T cells in the presence of the known immunosuppressant and the test compound; and, the denominator represents the NET RFU in the active T cells in the presence of only one of the known immunosuppressant and the test compound.

Once a compound has been identified as an immunosuppressive agent according to the present invention, the compound may be further tested and confirmed in animals and, in particular, in animal models of human immunopathological diseases such as, collagen induced arthritis (CIA), graft rejection, graft versus host disease (GVHD), etc.

Formulation and Administration of the Compositions: Effective concentrations of one or more of the immunosuppressive agents or pharmaceutically acceptable salts, or prodrugs thereof are mixed with a suitable pharmaceutical carrier or vehicle. In instances in which the compounds exhibit insufficient solubility, methods for solubilizing compounds may be used. Such methods are known to those of skill in this art, and include but are not limited to, using solubilizers, such as dimethylsulfoxide (DMSO), surfactants, such as polysorbate 80, dissolution in aqueous sodium bicarbonate, or use of transdermal penetration enhancers (e.g., AZONE™).

Upon mixing or adding the immunosuppressive compound(s) with a suitable carrier or vehicle, the resulting mixture may be a solution, suspension, emulsion or the like. The form of the resulting mixture depends upon a number of factors, including the intended mode of administration and the solubility of the compounds in the selected carrier or vehicle.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, bucally, intransally, orally, parenterally, intravenously, intradermally, subcutaneously, or topically, in liquid, semi-liquid, or solid form formulated in a manner suitable for each route of administration. Preferred modes of administration include oral, nasal and parenteral modes of administration.

The active compound is included in the pharmaceutically acceptable carrier in an amount sufficient to exert a therapeutically useful effect, preferably in the absence of undesirable side effects on the patient treated. The concentration of active compound in the drug composition will depend on absorption, inactivation and excretion rates of the active compound, the dosage schedule, and amount administered as well as other factors known to those of skill in the art.

Typically, a therapeutically effective dosage should produce a serum concentration of active ingredient from about 50–100 pg/ml to 0.1 mg/ml. The pharmaceutical composition typically should provide a dosage of from about 0.01 mg to about 10 mg of compound per kilogram of body weight per day. The active ingredient may be administered at once, or may be divided into a number of smaller doses to be administered at selected intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound may be provided in a composition that protects it from the acidic environment of the stomach. For example, the composition can be formulated in an enteric coating (e.g. with hydroxypropylmethyl cellulose phthalate) that maintains its integrity in the stomach and releases the active compound in the intestine (see *Remington's Pharmaceutical Sciences*, Osol, A., ed., Mack Publishing Co. (1980)). The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature; a binder, such as microcrystalline cellulose, gum tragacanth and gelatin; an excipient such as starch and lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials that modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active material can also be mixed with other active materials that do not impair the desired action, or with materials that supplement the desired action, such as antacids, H2 blockers, and antimetabolites. For example, if the compound is used for treating rheumatoid arthritis, it may be used with other immunosuppressive agents and/or analgesics or anti-inflammatory agents.

Solutions or suspensions used for parenteral, intradermal, subcutaneous, intranasal or topical application can include any of the following components: a sterile diluent, such as water for injection, saline solution, fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents such as ethylenediaminotetraacetic acid (EDTA); buffers, such as acetate, citrates, and phosphates; and agents for the adjustment of tonicity such as sodium chloride or dextrose. Parenteral preparations can be enclosed in ampoules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, lipsome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery system, and biodegradable, biocompatible polymers, such as collagen, ethylene vinyl acetate, polyanhydrides, polyglycolic acid, polyorthoesters, polylactic acid and others. The compounds may be dispersed throughout the carrier or encapsulated thereby. Methods for preparation of such formulations are known to those skilled in the art.

The compounds may be formulated for local or topical application, such as for topical application to the skin and mucous membranes, such as in the nose or eye, in the form of gels, creams, and lotions. The compounds may be formulated for application to the eye, or for intracisternal or intraspinal application in the form of solutions. Such solutions, particularly those intended for ophthalmic use, may be formulated as 0.01%–10% isotonic solutions, pH about 5–7, with appropriate salts. The compounds may be formulated as aerosols for topical application, such as by inhalation (see, e.g. U.S. Pat. Nos. 4,044,126, 4,414,209 and 4,364,923, which describe aerosols for delivery of a steroid useful for treating inflammatory diseases, particularly asthma).

The above listed drug administrative compounds or devices may be used in a method of treating an immunopathological disease comprising administering to an animal in need of such modulation an effective amount of an immunosuppressive agent, or a pharmaceutically acceptable salt or prodrug of an immunosuppressive agent identified according to the method described by the present invention. Moreover, the immunosuppressive agent may be first identified as an immunosuppressive agent in the method of the described invention.

Immunosuppressive agents may be packaged in kits for performing the method of treating an immunopathological disease. Such kits comprise packaging material and one or more containers therein such as bottles, jars, vials, ampules and the like, each of which containing an immunosuppressive agent, or a pharmaceutically acceptable salt or prodrug of the immunosuppressive agent. The packaging material would also include a label that indicates that the immunosuppressive agent, or a pharmaceutically acceptable salt or prodrug of the immunosuppressive agent, is useful to treat an immunopathological disease.

The following examples demonstrate usefulness of the invention in measuring the activity of caspases and other enzymes involved in apoptosis in cells and tissues. The examples also demonstrate usefulness of the invention in drug screening assays that can be utilized to find immunosuppressive agents. These examples are illustrative, but not limiting, of the method and compositions of the present invention. Other suitable modifications and adaptations of the variety of conditions and parameters normally encountered in in vitro assays and drug screening procedures or which are obvious to those skilled in the art are within the spirit and scope of the invention.

EXAMPLE 1

Identification of an immunosuppressive compound that exhibits caspase cascade activation only in activated T lymphocytes using a fluorogenic reporter molecule.

Human peripheral blood mononuclear cells (PBMC), were purchased from Clonetics, San Diego (cat. No. CC2702). These cells were primarily enriched in T lymphocytes by a process of leukapheresis and density gradient centrifugation (Clonetics), and contain some monocytes and no B lymphocytes or Dendritic cells. Cells are cultured ($0.75 \times 10^6$ cells/ml) in RPMI 1640 medium containing 10% fetal bovine serum (Gibco), 2 mM L-Glutamine, 25 mM Hepes, 1 mM sodium pyruvate, 1 mM non-essential aminoacids (NEAA) and 1% penicillin/streptomycin solution. Cells were then activated with 100 ng/ml of murine monoclonal antibody (OKT3) to the human T cell receptor (Liu, Y-C., et al., *J. Biol. Chem* 272: 9979 (1996)). Cells were incubated at 37° C. in a 5% $CO_2$-95% humidity incubator for 3 days. This resulted in optimal T cell activation as measured by the expression of the activation markers for IL2 receptor (CD25) and CD69 on the cells. These cells had >95% cell survival and were then used for the following experiments. In a parallel experiment, resting T lymphocytes that were not activated by the above method were used directly in an experiment. An aliquot of 45 µl of activated or resting T lymphocytes (containing $10^5$ cells) was added to a well of a 96-well microtiter plate containing 5 µl of a 10% DMSO in RPMI 1640 medium containing serial 2-fold dilution of the different test compounds starting at a concentration of 10 uM.

An aliquot of 45 µl of cells was also added to a well of a 96-well microtiter plate containing 5 µl of a 10% DMSO in RPMI 1640 medium without the test compounds as the control sample. The samples were gently mixed by agitation and then incubated at 37° C. for 24 hr in a 5% $CO_2$-95% humidity incubator. After incubation, the samples were removed from the incubator and 50 µl of a solution containing 20 µM of N-(Ac-DEVD)-N'-ethoxycarbonyl-R110 (SEQ ID NO. 1) fluorogenic substrate U.S. Pat. No. 6,342,611; WO 99/18856), 20 mM DTT(Sigma) in Hanks Balanced Salt Solution (HBSS, Gibco) was added. The samples were mixed by agitation and incubated for 1 hr at room temperature. Using a fluorescent plate reader (Model 1420, Wallac Instruments), an initial reading (T=0) was made approximately 1–2 mm after addition of the substrate solution, employing excitation at 485 nm and emission at 530 nm, to determine the background fluorescence of the control sample. After the 1 hr incubation, the samples were read for fluorescence as above (T=1 hr).

Calculation: Measured relative fluorescence unit (RFU) values were used to calculate the gain in fluorescence of the sample with the test compound as follows:

$$\text{Sample RFU}_{(T=1\ hr)} - \text{Sample RFU}_{(T=0)} = \text{Net Sample RFU} \quad (4)$$

and the background gain in fluorescence of the control sample (lacking the test compound) as follows:

$$\text{Control RFU}_{(t=1\ hr)} - \text{Control RFU}_{(t=0)} = \text{Net Control RFU} \quad (5)$$

The relative potency of a given test compound is given by the following ratio:

$$(\text{Net Sample RFU})/(\text{Net Control RFU}) \quad (6)$$

Note that a ratio in equation (6) greater than one suggests that the particular test compound induces apoptosis. A ratio equal, or nearly equal, to one indicates that the particular test compound had no net effect on apoptotic induction. Equations (4)–(6) are used to find a ratio for active T cells in the presence and absence of a test compound, and then sequentially for resting T cells both in the presence and absence of a test compound.

Several known caspase inducers were tested (see Table I below) and found that one of these compounds, (2-amino-3-cyano-7-dimethylamino-4-(3-bromo-4,5-dimethoxyphenyl)-4H-chromene, [CV58151]) induced apoptosis in activated T cells and not in resting T cells. Another compound, gambogic acid, induced apoptosis in both activated and resting T cells. An additional compound (5-(4-hydroxy-6-methyl-2H-pyran-2-one-3-yl)-7-(4-methylphenyl)-2,3,6,7-tetrahydro-1,4-thiazepine) did not induce apoptosis in either cell type. Table I summarizes the results. Note that for a given compound, when the ratio in the second column is greater than the ratio in the third column, then the compound selectively induces apoptosis in active T cells. Therefore this assay can be used for the discovery of compounds that selectively kill activated T lymphocytes.

TABLE I

| Compounds | Caspase Activity in Activated Cells 24 Hr Induction (Ratio) | Caspase Induction in Resting T Cells 24 Hr Induction (Ratio) |
|---|---|---|
| gambogic acid | 3.4 | 2.0 |
| 2-amino-3-cyano-7-dimethylamino-4-(3-bromo-4,5-dimethoxyphenyl)-4H-chromene (CV58151) | 2.2 | 0.9 |
| 5-(4-hydroxy-6-methyl-2H-pyran-2-one-3-yl)-7-(4-methylphenyl)-2,3,6,7-tetrahydro-1,4-thiazepine | 1.0 | 1.0 |

EXAMPLE 2

Identification of an immunosuppressive compound, that exhibits cytotoxicity in activated but not resting T lymphocytes using a chromogenic reporter molecule.

Human peripheral blood mononuclear cells (PBMC), were purchased from Clonetics, San Diego (cat. no. CC2702). These cells were primarily enriched in T lymphocytes by a process of leukapheresis and density gradient centrifugation (Clonetics), and contain some monocytes and no B lymphocytes or Dendritic cells. Cells are cultured ($0.75 \times 10^6$ cells/ml) in RPMI 1640 medium containing 10% fetal bovine serum (Gibco), 2 mM L-Glutamine, 25 mM Hepes, 1 mM sodium pyruvate, 1 mM non essential aminoacids (NEAA) and 1% penicillin/streptomycin solution. Cells were then activated with 100 ng/ml of murine monoclonal antibody to the human T cell receptor (Liu, Y-C., et al., *J. Biol. Chem.* 272: 9979 (1996)). Cells were incubated at 37° C. in a 5% $CO_2$-95% humidity incubator for 3 days. This resulted in optimal T cell activation as measured by the expression of the activation markers for IL2 receptor (CD25) and CD69 on the cells. These cells had >95% cell survival and were then used for the following experiments. In a parallel experiment, resting T lymphocytes that were not activated in the above mentioned method were used directly in an experiment.

An aliquot of 45 μl of activated or resting T lymphocytes (containing $10^5$ cells) was added to wells of a 96-well microtiter plate containing 5 μl of a 10% DMSO in RPMI 1640 medium containing different dilutions of the test compounds. An aliquot of 45 μl of activated or resting T cells ($10^5$ cells) was also added to wells of a 96-well microtiter plate containing 5 μl of a 10% DMSO in RPMI 1640 medium without the test compounds as the control sample. The samples were mixed by gentle agitation and then incubated at 37° C. for 48 hr in a 5% $CO_2$-95% humidity incubator. After incubation, the samples were removed from the incubator and 50 μl of a premixed dye solution was added (Promega cat. no. PRG3581). The samples were mixed by agitation and incubated for 1–4 hr at 37° C. in a 5% $CO_2$-95% humidity incubator. Using a plate reader (Model 1420, Wallac Instruments), samples were read at absorbance 490 nm.

Figure 2:
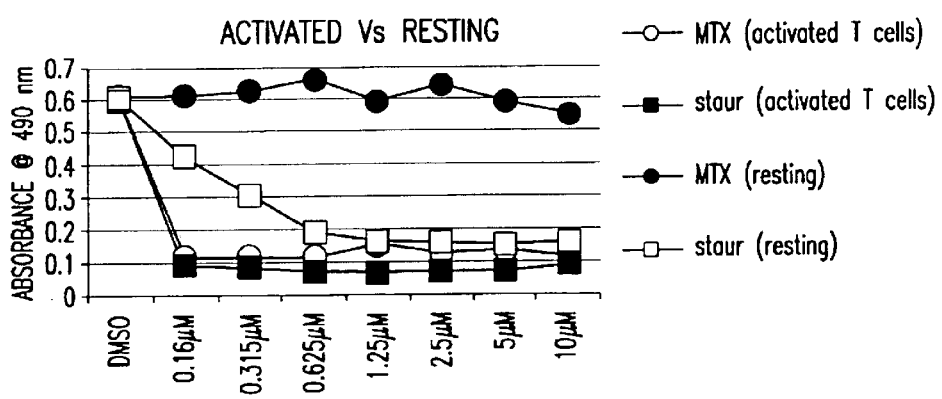
FIG. 2 depicts a graph showing the absorbance of a reporter molecule, of mitochondrial activity, as a function of methotrexate (MTX, circles) or staurosporine (squares) concentration in activated (open circles and filled in squares, respectively) and resting (filled in circles and open squares, respectively) T cells.

Some known apoptosis inducers were tested. As shown in FIG. 2, one of these compounds (staurosporine) is cytotoxic to both activated and resting T cells. As seen in FIG. 1 or 2, the other two compounds (methotrexate and 58151) are only cytotoxic to activated and not to resting T lymphocytes. Therefore this assay can be used for the identification of compounds that selectively induce apoptosis in activated T lymphocytes.

EXAMPLE 3

Effect Of CV58151 on CIA

Figure 3:
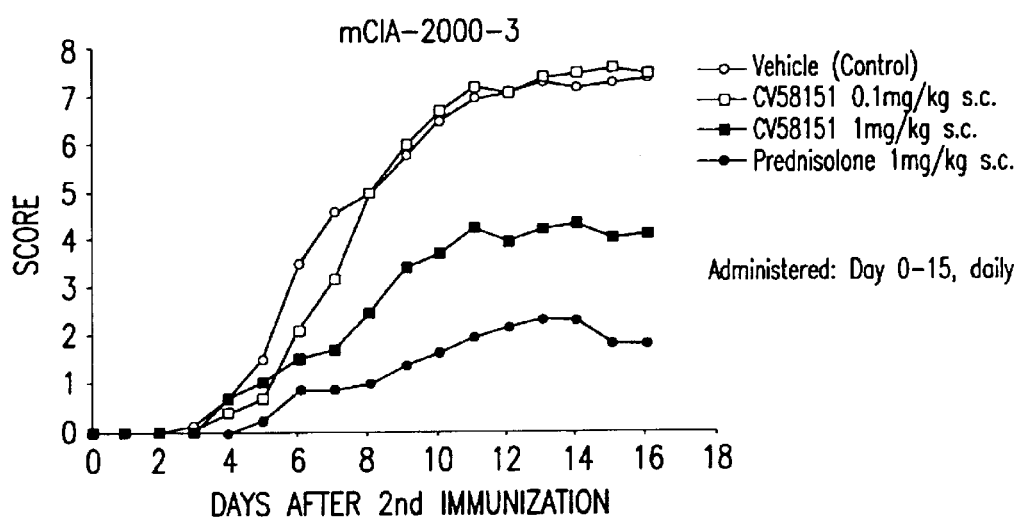
FIG. 3 depicts a graph showing the effect of test compound 2-amino-3-cyano-7-dimethylamino-4-(3-bromo-4,5-dimethoxyphenyl)-4H-chromene (CV58151) in a mouse model of collagen induced arthritis.

Collagen-induced arthritis (CIA), a model for rheumatoid arthritis (RA) in humans, is a chronic inflammatory arthropathy that can be induced in susceptible rodents by immunization with native type II collagen (CII). The development of arthritis is thought to be associated with the synergistic effect of high levels of cell-mediated and humoral immunity to CII. DBA/1 mice were immunized with type II collagen (100 μg/mouse) and Mycobacterium Tuberculosis (H37Ra) (100 μg/mouse) in Incomplete Freund's adjuvant (IFA) on Day 0 and repeated again on Day 21. Mice were administered drug subcutaneously with CV 58151 (0.1 mg/kg or 1 mg/kg) or a vehicle control (saline containing 2% DMSO and 2% Cremophor) daily from Day 21 through Day 35 and observed for the development of arthritis for 16 days after the $2^{nd}$ immunization (Days 21–36). Prednisolone was adminsistered in a separate group as a drug control with subcutaneous administration of 1 mg/kg daily starting at the time of the $2^{nd}$ immunization. The clinical severity of arthritis was quantified according to the following scoring system: 0, no change; 1, swelling and or erythema of one toe; 2, swelling and or erythema of two or more toes; 3, severe swelling and erythema of the entire paw and/or ankylosis. CIA score was expressed as the cumulative value for all paws, with a maximum possible score of 16. The results indicate that CV58151 at 1 mg/kg was effective in reducing CIA by a decrease in the cumulative score by 50% (FIG. 3). In comparison predisolone reduced the cumulative score by 75%. CV58151 with this administration is effective at reducing collagen induced arthritis.

EXAMPLE 4

Effect Of CV58151 on ConA Induced Hepatitis

Figure 4:
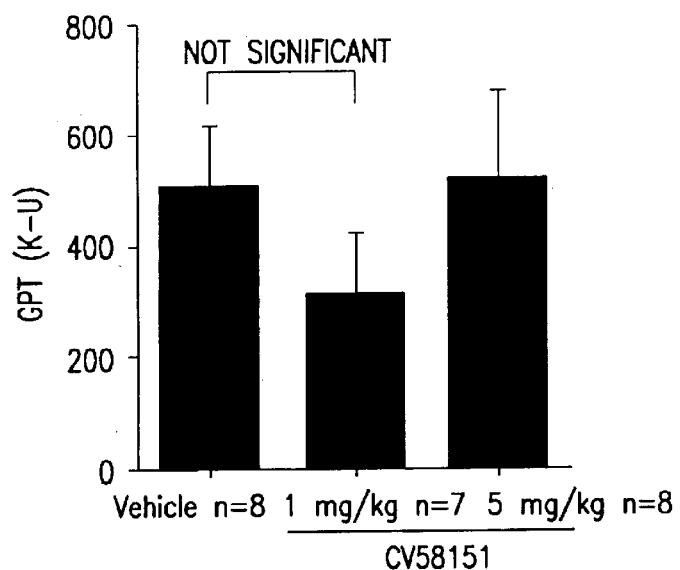
FIG. 4 depicts a graph showing the effect of test compound 2-amino-3-cyano-7-dimethylamino-4-(3-bromo-4,5-dimethoxyphenyl)-4H-chromene (CV58151) in a mouse model of liver injury due to concanavalin A.

Concanavalin A (ConA) activates T lymphocytes and in mice induces hepatic injury characterized by apoptotic and necrotic cell death (Tiegs et al., J. Clin. Invest. 90:196, 1992). C3H/HeN mice were administered intraperitoneally with either 5 mg/kg or 1 mg/kg CV58151 in saline containing 2% DMSO and 2% Cremophor. One hour later, animals were challenged with 0.5 mg/mouse ConcanavalinA (ConA) by intravenous injection. Control animals received only the compound vehicle. 24 hrs later blood samples were collected and analysed for glutamate-pyruvate transaminase/glutamic-pyruvic transaminase (GPT). As shown in FIG. 4, administration of the compound, under these conditions, did not reduce liver damage as indicated by GPT enzyme levels.

EXAMPLE 5

Effect Of CV58151 on PLP-EAE

Figure 5:
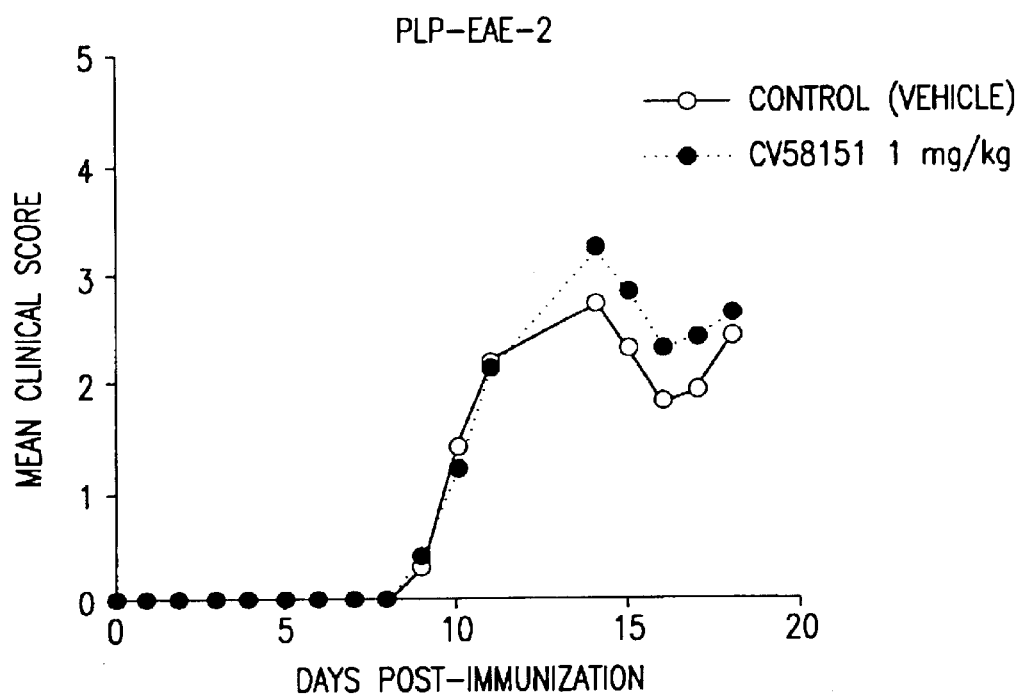
FIG. 5 depicts a graph showing the effect of test compound 2-amino-3-cyano-7-dimethylamino-4-(3-bromo-4,5-dimethoxyphenyl)-4H-chromene (CV58151) in a mouse model of experimental autoimmune encephalomyelitis.

Experimental autoimmune encephalomyelitis (EAE) is an inflammatory demyelinating disease of the central nervous system (CNS) and can be induced by inoculation of animals with homogenized CNS tissue or highly purified myelin proteins such as myelin basic protein (MBP) or proteolipid protein (PLP). It is widely studied as a possible animal model of multiple sclerosis. On Day 0, proteolipid protein (PLP) (150 μg/mouse) and Mycobacterium Tuberculosis (H37Ra) (200 μg/mouse) in Incomplete Freund's adjuvant (IFA) was administered sub-cutaneously and pertussis toxin (PTX) (200 ng/mouse) was administered intraperitoneally to SJL mice. On Day 2, PTX (200 ng/mouse) seas injected intraperitoneally. On Days 0 through 11, CV 58151 (1 mg/kg) in saline containing 2% DMSO and 2% Cremophor was administered subcutaneously once a day. The mean clinical scores was quantified according to the following scoring system: 0, no clinical signs; 1, loss of tail tonicity; 2, impaired righting reflex; 3, hind leg paralysis; 4, hind and foreleg paralysis; 5, death. The results indicated that, with this amount and administration schedule, CV58151 did not reduce PLP induced EAE (FIG. 5).

EXAMPLE 6

Effect Of CV58151 on mBSA-DTH

Figure 6:
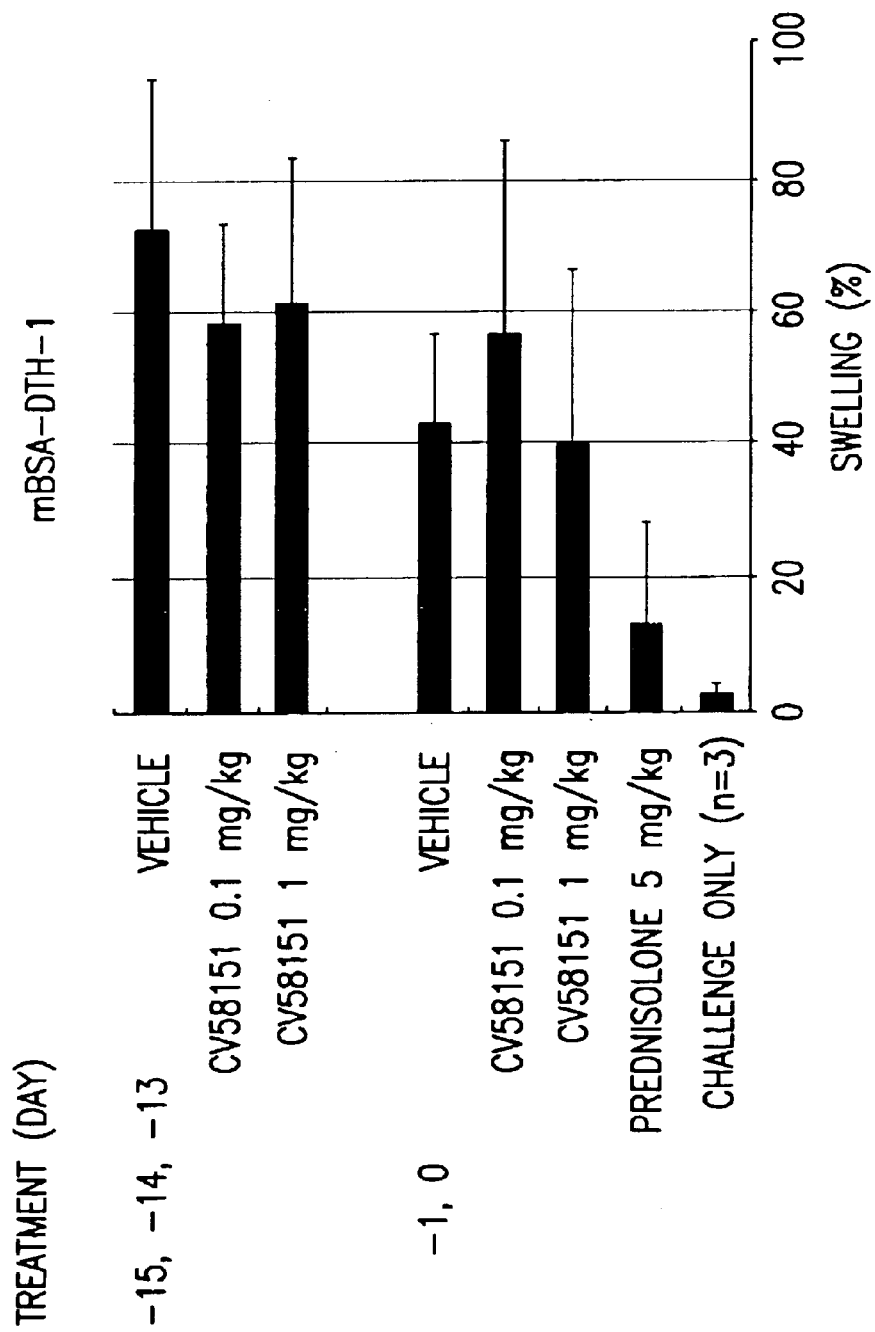
FIG. 6 depicts a graph showing the effect of test compound test compound 2-amino-3-cyano-7-dimethylamino-4-(3-bromo-4,5-dimethoxyphenyl)-4H-chromene (CV58151) in a mouse model of delayed-type hypersensitivity.

Many drugs and other chemicals can alter cell-mediated immune response (CMI), a response that often correlates with delayed-type hypersensitivity (DTH). The effects of various antigens, adjuvants, doses, routes, and immunosuppressants are investigated in DTH models and correlate with CMI modulation. The DTH model used here examined footpad swelling reaction elicited by certain preparations of bovine serum albumin (BSA) and Complete Freund's adjuvant (CFA) Methylated BSA+ CFA (50% saline containing 12.5 mg/ml methylated BSA and 2.5 mg/ml dextran, 50% IFA) was injected (100 µl per mouse) subcutaneously on Day −15 to sensitize the BDF1 mice. Day 0 is day of challenge where 50 µl of a saline solution containing 20 µg of methylated BSA and 50 µg of alum were injected into the right foot pad. Treatment with CV58151 was carried out in two groups with doses of 0.1 mg/kg and 1 mg/kg given once a day subcutaneously. One group received CV58151 or vehicle control once a day on Days −15, −14, and −13. Another group received CV58151 or vehicle control once a day on Day −1 and Day 0 at 1 hr after the challenge. Prednisolone, 5 mg/kg, was included in the second group as a drug control and injected subcutaneously. On Day 0 and Day 1, the right footpad thickness was measured with a pressure caliper and the % swelling determined (FIG. 6). The results indicated that CV58151, with these amounts and administration schedule, did not reduce footpad swelling.

Having described preferred embodiments of the invention, it is to be understood that the invention is not limited to those precise embodiments, and that the various changes and modifications may be effected therein by one skilled in the art without departing from the scope or spirit of the invention as defined in the appended claims. Thus, the scope of the invention should be determined by the appended claims and their legal equivalents, rather than by the examples given. All patents, patent applications and publications referred to herein are incorporated by reference in their entirety.

What is claimed is:

1. A method for identifying an immunosuppressive agent comprising:

(a) obtaining at least one sample of viable cultured active T cells having intact cell membranes from a cell growth medium under conditions conducive to growth;

(b) combining a first portion of said at least one sample with a predetermined amount of at least one test compound dissolved in a solvent for a predetermined period of time at a predetermined temperature thereby generating a first volume;

(c) combining a second portion of said at least one sample with an amount of the solvent which was used to dissolve said at least one test compound, for said predetermined period of time at said predetermined temperature thereby generating a second volume;

(d) separately adding to each of said first volume and said second volume a cell permeable reporter compound having at least one measurable property which is responsive to the caspase cascade, wherein said reporter compound comprises
  (i) a caspase substrate; and
  (ii) a fluorogenic or fluorescent moiety, whereby said at least one measurable property is a change in fluorescence;

(e) measuring said at least one measurable property of said reporter compound in said first volume and thereby measuring the caspase cascade activity of said first volume;

(f) measuring said at least one measurable property of said reporter compound in said second volume and thereby measuring the caspaso cascade activity of said second volume;

(g) calculating a first ratio of caspase cascade activity measured for said first volume to said caspase cascade activity measured for said second volume, wherein when the first ratio is greater than one, said at least one test compound kills active T cells and is identified as a potential immunosuppressive agent.

2. The method of claim 1, further comprising:
   (a) obtaining at least one sample of viable cultured resting T cells having intact cell membranes from a cell growth medium under conditions conducive to growth;
   (b) combining said resting T cells with said predetermined amount of said identified immunosuppressive agent dissolved in said solvent for said predetermined period of time at said predetermined temperature thereby generating a third volume;
   (c) adding to said third volume said reporter compound having at least one measurable property which is responsive to the caspase cascade;
   (d) measuring said at least one measurable property of said reporter compound in said third volume and thereby measuring the caspase cascade activity of said third volume; and,
   (e) calculating a second ratio of caspase cascade activity measured for said first volume to said caspase cascade activity measured for said third volume, wherein when the second ratio is greater than one, then said identified immunosuppressive agent is further identified as an active-T-cell-selective immunosuppressive agent.

3. The method of claim 1 or 2, wherein said at least one test compound is applied to the T cells at a concentration in the range from about 1 picomolar to about 1 millimolar.

4. The method of claim 1 or 2, further comprising adding a permeabilization enhancer in combination with said reporter compound.

5. The method of claim 1 or 2, wherein said predetermined period of time is about 1 minute to about 48 hours; and wherein said predetermined temperature is about 4° C. to about 42° C.

6. The method of claim 5, wherein said predetermined period of time is about 24 hours to about 48 hours.

7. The method of claim 1, wherein a plurality of viable cultured active T cell samples are exposed separately to a plurality of test compounds, 8. The method of claim 2, wherein a plurality of viable cultured resting T cell samples are exposed separately to a plurality of test compounds.

9. The method of claim 7 or 8, wherein said plurality of viable cultured T cell samples are in separate wells of a microtiter plate.

10. The method of claim 1, wherein said active T cells are obtained by adding to T cells antibodies to the T cell receptor, Concanavalin A, or Phytohaemagglutinin.

11. The method or claim 2 or 8, wherein said active T cells are obtained from tissue of a patient afflicted with one or more immunopathological symptoms and wherein said resting T cells are from healthy tissue that is not afflicted with the immunopathological symptoms.

12. A method for assaying the potency of a test compound to synergise with a known immunosuppressant by functioning as an activator of the caspase cascade, said method comprising:
   (a) obtaining at least one of viable cultured active T cells having intact cell membranes by culturing T cells in a cell growth medium under conditions conducive to growth and activating the cells;
   (b) exposing a first portion of said at least one sample to a combination of a predetermined amount of said test compound and a subinducing amount of said known immunosuppressant for a first predetermined period of time, at a first predetermined temperature thereby generating a first volume;
   (c) exposing a second portion of said at least one sample to an amount of solvent which was used to dissolve the test compound and to said subinducing amount of said known immunosuppressant for said first predetermined period of time at said first predetermined temperature thereby generating a second volume;
   (d) adding a cell permeable reporter compound to said first volume and to said second volume, said reporter compound having at least one measurable property which is responsive to the caspase cascade, wherein said reporter compound comprises
      (i) a caspase substrate; and
      (ii) a fluorogenic or fluorescent moiety, whereby said at least one measurable property is a change in fluorescence;
   (e) incubating the resulting mixture of said first volume with said reporter compound for a second predetermined time period at a second predetermined temperature;
   (f) incubating the resulting mixture of said second volume with said reporter compound for said second predetermined time period at said second predetermined temperature;
   (g) measuring said at least one measurable property of said reporter compound in each of said resulting mixtures and thereby measuring the caspase cascade activity of said first volume and of said second volume; and,
   (h) calculating the ratio of measured caspase cascade activities of said first volume to said second volume to determine whether said test compound synergises with said known immunosuppressant as an activator of the caspase cascade.

13. The method of claim 12, wherein a plurality of populations of viable cultured active T cell samples are exposed separately to a plurality of test compounds.

14. The method of claim 12, wherein said plurality of populations of viable cultured active T cell samples are in separate wells of a microtiter plate.

15. A method for identifying an immunosuppressive agent comprising:
   (a) obtaining a sample of viable cultured active T cells having an intact cell membrane;
   (b) obtaining a sample of viable cultured resting T cells having an intact cell membrane;
   (c) separately exposing the active and resting T cell samples to at least one test compound for a predetermined period of time under predetermined conditions;
   (d) adding a cell permeable reporter compound having at least one measurable property which is responsive to the caspase cascade to the active and resting T cells that have been exposed to the at least one test compound, wherein said reporter compound comprises
      (i) a caspase substrate; and
      (ii) a fluorogenic or fluorescent moiety, whereby said at least one measurable property is a change in fluorescence;
   (e) measuring the caspase cascade activity in the active T cells exposed to the at least one test compound by measuring said at least one measurable property; and
   (f) measuring the caspase cascade activity in said resting T cells exposed to the at least one test compound by measuring said at least one measurable property, wherein when the caspase cascade activity in the active T cells is greater than the caspase cascade activity in the resting T cells, the at least one test compound selectively kills active T cells and is an immunosuppressive agent.

16. The method of claim 12 or 15, wherein said at least one test compound is applied to the T cells at a concentration in the range from about 1 picomolar to about 1 millimolar.

17. The method of claim 12 or 15, further comprising adding a permeabilization enhancer in combination with said reporter compound.

18. The method of claim 12 or 15, wherein said predetermined period of time is about 1 minute to about 48 hours; and wherein said predetermined temperature is about 4° C. to about 42° C.

19. The method of claim 18, wherein said predetermined period of time is about 24 hours to about 48 hours.

20. The method of claim 15, wherein a plurality of viable cultured active T cell samples are exposed separately to a plurality of test compounds.

21. The method of claim 15, wherein a plurality of viable cultured resting T cell samples are exposed separately to a plurality of test compounds.

22. The method of claim 20 or 21, wherein said plurality of viable cultured cells are in separate wells of a microtiter plate.

23. The method of claim 12 or 15, wherein said active T cells are obtained by adding to T cells antibodies to the T cell receptor, Concanavalin A, or Phytohaemagglutinin.

24. The method of claim 15 or 21, wherein said active T cells are obtained from tissue of a patient afflicted with one or more immunopathological symptoms and wherein said resting T cells are from healthy tissue that is not afflicted with the immunopathological symptoms.

* * * * *